United States Patent [19]

Bormann et al.

[11] 4,201,779

[45] May 6, 1980

[54] 7[(2-AMINO-THIAZOL-4-yl) GLYOXYLAMIDO]-CEPHEM DERIVATIVES AND PROCESSES FOR THEIR PREPARATION

[75] Inventors: Dieter Bormann; Bernd Knabe, both of Kelkheim; Elmar Schrinner; Manfred Worm, both of Wiesbaden, all of Fed. Rep. of Germany

[73] Assignee: Hoechst Aktiengesellschaft, Frankfurt am Main, Fed. Rep. of Germany

[21] Appl. No.: 884,813

[22] Filed: Mar. 9, 1978

[30] Foreign Application Priority Data

Mar. 12, 1977 [DE] Fed. Rep. of Germany ....... 2710902

[51] Int. Cl.² ................. C07D 501/46; C07D 501/22; C07D 501/36; A61K 31/545
[52] U.S. Cl. ........................................ 424/246; 544/8; 544/21; 544/27; 544/28; 548/194
[58] Field of Search ...................... 544/21, 27, 28, 8; 424/246

[56] References Cited

U.S. PATENT DOCUMENTS

| | | | |
|---|---|---|---|
| 4,008,246 | 2/1977 | Ochiai et al. | 544/28 |
| 4,098,888 | 7/1978 | Ochiai et al. | 544/21 |
| 4,132,789 | 2/1979 | Nomura et al. | 544/27 |

FOREIGN PATENT DOCUMENTS 1208014 10/1970 United Kingdom .
1208015 10/1970 United Kingdom .

Primary Examiner—Mark L. Berch
Attorney, Agent, or Firm—Curtis, Morris & Safford

[57] ABSTRACT

Cephem derivatives of the formula

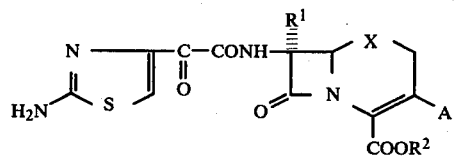

in which $R^1$ denotes hydrogen or low-molecular alkoxy, $R^2$ denotes hydrogen, optionally substituted alkyl, phthalide or a cation, X denotes sulfur, oxygen or $CH_2$ and A denotes hydrogen, alkoxy, halogen or a group —$CH_2Y$, in which Y represents hydrogen, acyloxy, alkoxy, optionally substituted carbamoyloxy or a group —$SR^3$, in which $R^3$ can represent acyl, alkyl or an optionally substituted 5-membered or 6-membered heterocyclic structure are disclosed as valuable antibiotics which are well suited for combating Gram-positive and in particular Gram-negative infections and also have an unexpectedly good action against penicillinase-forming staphylococci.

5 Claims, No Drawings

7[(2-AMINO-THIAZOL-4-YL)GLYOXYLAMIDO]-CEPHEM DERIVATIVES AND PROCESSES FOR THEIR PREPARATION

The invention relates to cephem derivatives of the general formula I

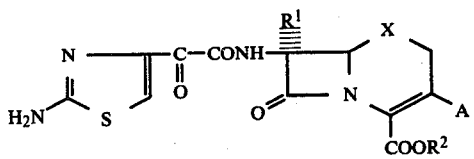

in which $R^1$ denotes hydrogen or low-molecular alkoxy, $R^2$ denotes hydrogen, optionally substituted alkyl, phthalide or a cation, X denotes sulfur, oxygen or $CH_2$ and A denotes hydrogen, alkoxy, halogen or a group $-CH_2Y$, in which Y represents hydrogen, acyloxy, alkoxy, optionally substituted carbamoyloxy or a group $-SR^3$, in which $R^3$ can represent acyl, alkyl or an optionally substituted 5-membered or 6-membered heterocyclic structure.

The invention also relates to the process for the preparation of compounds of the general formula I, which comprises reacting lactams of the general formula II

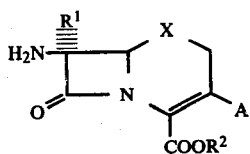

in which $R^1$, $R^2$, A and X have the abovementioned meanings but $R^2$ cannot represent hydrogen, with reactive derivatives of a carboxylic acid of the general formula III

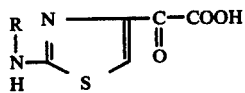

in which R denotes a protective group, and converting the resulting products of the general formula IV

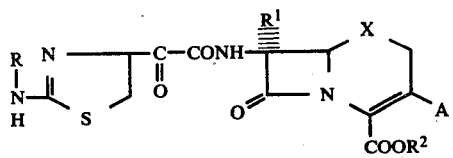

in which the radicals R, $R^1$, $R^2$, X and A have the meanings given initially, into the compounds of the general formula I.

The invention also relates to the compounds of the general formula III and the process for the preparation of these compounds, which comprises halogenating acetoglyoxylic acid esters, subsequently reacting the resulting product with thiourea to give a (2-amino-thiazol-4-yl)-glyoxylic acid ester of the general formula V, converting the latter to derivatives of the general formula VI by introducing a protective group R and then saponifying these derivatives to the carboxylic acids of the general formula III

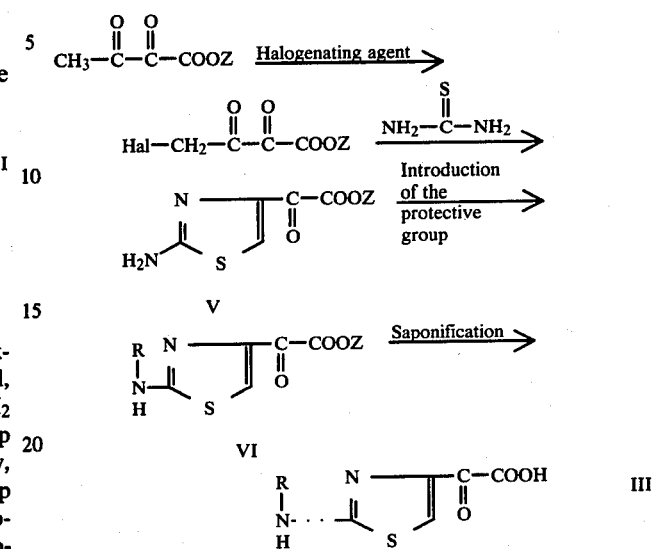

In these formulae Z represents the radical of an alcohol, preferably of a low-molecular aliphatic alcohol and Hal represents halogen, especially bromine and chlorine.

$R^1$ can denote low-molecular alkoxy, such as methoxy, ethoxy, propoxy or butoxy, but especially hydrogen.

Amongst the definitions given above for X, the preferred meaning is that of a sulfur atom.

If the radical A in the general formula represents alkoxy, possible groups are, for example, low-molecular groups having 1 to 4 C atoms, such as, for example, methoxy, ethoxy or butoxy, especially methoxy and ethoxy, but preferably the methoxy group.

If A represents halogen, possible halogens are in particular chlorine and bromine.

Preferably, the radical A represents the group $-CH_2Y$, in which Y can have the following meanings.

If Y represents acyloxy, possible radicals are, for example, low-molecular acyloxy radicals, such as, for example, acetoxy or propionyloxy. The acetoxy radical is particularly preferred.

If Y represents alkoxy, possible radicals are straight-chain or branched alkoxy radicals having, for example, 1-8 C atoms and preferably 1-4 C atoms, such as, for example, methoxy, ethoxy, n-propoxy, iso-propoxy, n-butoxy or iso-butoxy.

If Y represents a carbamoyloxy group, this group can be monosubstituted or polysubstituted on the nitrogen, for example by low-molecular alkyl groups, such as, for example, methyl or ethyl, and the two substituents can also be bonded with one another to form a ring, for example to give a 5-membered or 6-membered ring, which can also be interrupted by a hetero-atom, such as, for example, oxygen, sulfur or nitrogen. However, the unsubstituted carbamoyloxy group is preferred.

If Y represents a group $SR^3$ and if $R^3$ represents an acyl radical, possible radicals are, for example, low-molecular acyl radicals. The acetyl and propionyl radicals, especially the acetyl radical, are preferred.

If $R^3$ denotes an alkyl radical, possible radicals are straight-chain or branched alkyl radicals having, for example, 1-8 C atoms and preferably 1-4 C atoms, such as, for example, methyl, ethyl, n-propyl, iso-propyl, n-butyl or isobutyl, especially methyl and ethyl, which can optionally be substituted by amino, hydroxyl or low-molecular carbalkoxy, especially carbomethoxy, or by phenyl which is optionally substituted by low-molecular alkyl or alkoxy, nitro or halogen, especially chlorine or bromine, or by carboxyl groups.

If $R^3$ is a heterocyclic structure, possible structures are optionally substituted five-membered or six-membered, preferably five-membered, rings, which in the case of the 5- membered rings possess 1 to 4 heteroatoms, such as oxygen, sulfur and/or nitrogen, especially nitrogen, optionally together with sulfur, as ring atoms.

The heterocyclic ring system which forms the radical $R^3$ can also be wholly or partially hydrogenated but is preferably not hydrogenated.

The following basic ring systems may be mentioned as examples of the radical $R^4$: thienyl, furanyl, pyrrolyl, imidazolyl, pyrazolyl, thiazolyl, isothiazolyl, oxazolyl, isoxazolyl, triazolyl, thiadiazolyl, oxadiazolyl, tetrazolyl, thiatriazolyl, oxatriazolyl, pyridyl, pyrimidyl, pyrazinyl, pyridazinyl, thiazinyl, oxazinyl, triazinyl, thiadiazinyl, oxadiazinyl, dithiazinyl, dioxazinyl, oxathiazinyl, tetrazinyl, thiatriazinyl, oxatriazinyl, dithiadiazinyl, imidazolinyl and tetrahydropyrimidyl.

Amongst the ring systems listed by way of example above, preferred systems are 5-membered ring systems with 1 to 2 nitrogen atoms and optionally one oxygen atom, such as, for example, oxazolyl, preferably oxazol-2-y1, oxadiazolyl and imidazolinyl, preferably imidazolin-2-y1, and 6-membered ring systems with 1 to 3, preferably 1 to 2 and especially one nitrogen atom and optionally one sulfur atom, such as, for example, pyridyl, such as pyrid-2-y1, pyrid-3-yl and pyrid-4-yl, pyrimidyl, preferably pyrimid-2-yl and pyrimid-4-yl, tetrahydropyrimidyl, preferably 1,4,5,6-tetrahydropyrimid-2-yl, thiadiazinyl, especially 4H-1,3,4-thiadiazin-2-yl, triazinyl, preferably 1,3,4-triazin-2-yl and 1,3,5-triazin-4-yl, and pyridazinyl, especially pyridazin-3-yl. The pyridyl radicals are preferred.

Particularly preferred ring systems are 5-membered ring systems with one sulfur atom and 1 to 2 nitrogen atoms, such as thiazolyl, especially thiazol-2-yl, thiadiazolyl, especially 1,3,4-thiadiazol-5-yl and 1,2,4-thiadiazol-5-yl, 5-membered ring systems with 3 to 4 nitrogen atoms, such as triazolyl, preferably 4H-1,2,4-triazol-3-yl and tetrazolyl, preferably 1H-tetrazol-5-yl, and also the 1,3,4-oxadiazol-5-yl system. Derivatives which can be used according to the invention are in particular the tetrazolyl derivatives.

When it denotes a heterocyclic structure, the radical $R^3$ can be monosubstituted or polysubstituted, possible substituents being, for example, those which follow: aklyl groups having, for example, 1 to 8 carbon atoms, such as, for example, methyl ethyl, n-propyl, isopropyl, n-butyl, tert.-butyl, n-hexyl and octyl, preferably those having 1 to 4 carbon atoms, especially methyl, and low-molecular alkyl groups having 1 to 4 carbon atoms, preferably methyl, which are substituted, for example by low-molecular alkoxycarbonyl, such as, for example, methoxycarbonyl or ethoxycarbonyl, carboxyl, sulfo groups or low-molecular alkoxysulfonyl, such as, for example, methoxysulfonyl or ethoxysulfonyl, or by halogen, such as, for example, chlorine or bromine.

When it denotes a heterocylic structure, $R^3$ can also be substituted by cycloalkyl groups, such as, for example, cyclopentyl and cyclohexyl, or by low-molecular alkoxy groups, such as, for example, methoxy and ethoxy, low-molecular alkenyl groups, such as, for example, allyl, low-molecular alkylmercapto and alkenylmercapto groups, such as, for example, methylmercapto and allylmercapto, low-molecular alkoxycarbonyl, such as, for example, methoxycarbonyl, low-molecular alkoxycarbonylamino, such as, for example, ethoxycarbonylamino, low-molecular carboxyalkylthio, such as, for example, carboxymethylthio, amino, low-molecular mono- and di-alkylamino, such as, for example, methylamino, dimethylamino, ethylamino and diethylamino, oxido, hydroxyl, nitro, cyano, halogen, preferably chlorine, mercapto, carboxyl, aryl radicals, such as, for example, phenyl, substituted phenyl, such as, for example, low-molecular alkoxyphenyl, such as methoxyphenyl and ethoxyphenyl, halogenophenyl, such as, for example, chlorophenyl, hydroxyphenyl, aminophenyl, alkylphenyl, especially low-molecular alkylphenyl, such as tert.-butylphenyl, tolyl, cetylphenyl, nitrophenyl and biphenyl, or pyridyl, methylpyridyl, furyl, naphthyl, quinolyl, isoquinolyl, thienyl, 2-thiazolyl, 2-pyrrolyl, 4-imidazolyl, 5-pyrazolyl and 4-isoxazolyl.

When they denote a heterocyclic structure, preferred radicals $R^3$ according to the invention are the unsubstituted radicals and also the heterocyclic radicals $R^3$ which are substituted by straight-chain or branched alkyl having 1 to 8 carbon atoms, especially low-molecular alkyl, preferably methyl, and also by aryl, especially phenyl, which can optionally be substituted by low-molecular alkyl or alkoxy groups, nitro groups or halogen, especially chlorine or bromine. Particularly preferred possible radicals are the heterocyclic 5-membered rings substituted by low-molecular alkyl.

Specific examples of the radical $R^3$ which may be mentioned are, in particular, those which follow: 1H-1,2,3-triazol-5-yl, 1,2,4-triazol-3-yl, 5-methyl-1,2,4-triazol-3-yl, 1-phenyl-3-methyl-1H-1,2,4-triazol-5-yl, 4,5-dimethyl-4-H-1,2,4-triazol-3-yl, 5-methyl-4-amino-4H-1,2,4-triazol-3-yl, 4-phenyl4H-1,2,4-triazol-3-yl, 5-ethyl-1,2,4-triazol-3-yl, 4-amino-4H-1,2,4-triazol-3-yl, 5-ethyl-4-amino-4-H-1,2,4-triazol-3-yl, 5-phenyl-1,2,4-triazol-3-yl, 5-(4-methoxyphenyl)-1,2,4-triazol-3-yl, 5-(4-chlorophenyl)-1,2,4-triazol-3-yl, 5-(4-pyridyl)-1,2,4-triazol-3-yl, 5-(4-chlorophenyl)-1,2,4-triazol-3-yl, 5-(4-pyridyl)-1,2,4-triazol-3-yl, 5-[4-(2-methyl-pyridyl)-]-1,2,4-triazol-3-yl, 5-phenoxymethyl-1,2,4-triazol-3-yl, 5-methoxymethyl 5-ethoxymethyl-1,2,4-triazol-3-yl, 5-ethoxycarbonylmethyl-1,2,4-triazol-3-yl, 5-(2-ethoxyethyl)-1,2,4-triazol-3-yl, 5-(2-aminoethyl)-1,2,4-triazol-3-yl, 4-methyl-5-phenyl-4H-1,2,4-triazol-3-yl, 4-(4-ethoxyphenyl)-5-(4-pyridyl)-4H-1,2,4-triazol-3-yl, 4-(4-methoxyphenyl)-5-(4-pyridyl)-4H- 1,2,4-triazol-3-yl, 4-(4-ethoxyphenyl)-5-(3-pyridyl)-4H-1,2,4- triazol-3-yl, 4-(4-ethoxyphenyl)-5-phenyl-4H-1,2,4-triazol-3-yl, 4-(4-ethoxyphenyl)-5-(4-aminophenyl)-4H-1,2,4-triazol-3-yl, 4,5-diphenyl-4H-1,2,4-triazol-3-yl, 4,5-di-p-tolyl-4H-1,2,4-triazol-3-yl, 4-allyl-5-phenyl-4H-1,2,4-triazol-3-yl, 4-amino-5-methyl-4H-1,2,4-triazol-3-yl, 4-amino-5-ethyl-4H-1,2,4-triazol-3yl, 1-methyl-5-phenyl-1,2,4-triazol-3-yl, 1-phenyl-4-allyl-5-(m-nitrophenyl)-4H-1,2,4-triazol-3-yl, 1-phenyl-4-allyl-5-t-butyl-4H -1,2,4-triazol-3-yl, 1H-tetrazol-5-yl, 1methyl-1H-tetrazol-5-yl, 1-ethyl-1H-tetrazol-5-yl, 1-n-propyl-1H-tetrazol-5-yl, 1-i-propyl-1H-tetrazol-5-yl, 1-n-butyl-1H-tetrazol-5yl, 1-cyclopentyl-1H-tetrazol-5-yl, 1-phenyl-1H-tetrazol-5-yl, 1-p-chlorophenyl-1H-tetrazol-5-yl, 1-cyclohexyl-1H-tetrazol-5-yl, 1-benzyl-1H-tetrazol-5-yl, 1-allyl-1H- tetrazol-5-yl, 1,2,3-thiadiazol-5-yl, 1,3,4-thiadiazol-2-yl, 1,2,4-thiadiazol-3-yl, 1,2,4-thiadiazol-5-yl, 1,2,5-thiadiazol-3-yl, 3-methyl-1,2,4-thiadiazol-5-yl, 3-phenyl-1,2,4-thiadiazol-5-yl, 2-methyl-1,3,4-thiadiazol-5-yl, 2-methylmercapto-1,3,4-thiadiazol-5-yl, 2-ethyl-1,3,4-thiadiazol-5-yl, 2-n-propyl-1,3,4-thiadiazol-5-yl, 2-i-propyl-1,3,4-thiadiazol-5-yl, 2-phenyl-1,3,4-thiadiazol-5-yl, 2-(4-methoxyphenyl)-1,3,4-thiadiazol-5-yl, 2-(4-chlorophenyl)-1,3,4-thiadiazol-5-yl, 2-n-heptyl-1,3,4-thiadiazol-5-yl, 2-(2-furyl)-1,3,4-thiadiazol-5-yl, 2-(3-pyridyl)-1,3,4-thiadiazol-5-yl, 2-n-butyl-1,3,4-thiadiazol-5-yl, 2-(2-pyridyl)-1,3,4-thiadiazol-5-yl, 2-(4-pyridyl)-1,3,4-thiadiazol-5-yl, 2-(1-naphthyl)-1,3,4-thiadiazol-5-yl, 2-(2-quinolyl)-1,3,4-thiadiazol-5-yl, 2-(1-isoquinolyl)-1,3,4-thiadiazolyl-5-yl, 2-ethoxycarbonylmethyl-1,3,4-thiadiazol-5-yl, 2-phenyl-3-methyl-1,3,4-thiadiazol-5-yl, 2-ethoxycarbonylamino-4-methyl-1,3,4-thiadiazol-5-yl, 3-methylmercapto-1,2,4-thiadiazol-5-yl, 1,2,4-oxadiazol-5-yl, 1,2,3-oxadiazol-5-yl, 1,3,4-oxadiazol-5-yl, 2-methyl-1,3,4-oxadiazol-5-yl, 2-ethyl-1,3,4-oxadiazol-5-yl, 2-phenyl-1,3,4-oxadiazol-5-yl, 2-(4-nitrophenyl)-1,3,4-oxadiazol-5-yl, 2-(2-thienyl)-1,3,4-oxadiazol-5-yl, 2-(3-thienyl)-1,3,4-oxadiazol-5-yl, 2-(4-chlorophenyl)-1,3,4-oxadiazol-5-yl, 2-(2-thiazolyl)-1,3,4-oxadiazol-5-yl, 2-(2-furyl)-1,3,4-oxadiazol-5-yl, 2-(4-pyridyl)-1,3,4-oxadiazol-5-yl, 2-(3-nitrophenyl)-1,3,4-oxadiazol-5-yl, 2-(2-methoxyphenyl)-1,3,4-oxadiazol-5-yl, 2-(2-tolyl)-1,3,4-oxadiazol-5-yl, 2-(3-tolyl)-1,3,4-oxadiazol-5-yl, 2-(2-hydroxyphenyl)-1,3,4-oxadiazol-5-yl, 2-(4-hydroxyphenyl)-1,3,4-oxadiazol-5-yl, 2-n-butyl-1,3,4-oxadiazol-5-yl, 2-n-propyl-1,3,4-oxadiazol-5-yl, 2-benzyl-1,3,4-oxadiazol-5-yl, 2-(1-naphthyl)-1,3,4-oxadiazol-5-yl, 2-(2-pyrrolyl)-1,3,4-oxadiazol-5-yl, 2-(4-imidazolyl)-1,3,4-oxadiazol-5-yl, 2-(5-pyrazolyl)-1,3,4-oxadiazol-5-yl, 2-(3,5-dimethyl-4-isoxazolyl)-1,3,4-oxadiazol-5-yl, thiazol-2-yl, 4-methylthiazol-2-yl, 4-phenyl-thiazol-2-yl, 4-pentyl-thiazol-2-yl, 4-hexyl-thiazol-2-yl, 4-undecylthiazol-2-yl, 4-tridecyl-thiazol-2-yl, 4-pentadecyl-thiazol-2-yl, 4-p-tert-butylphenyl-thiazol-2-yl, 4-p-cetylphenyl-thiazol-2-yl, 4-p-phenylphenyl-thiazol-2-yl, 4-ethyl-thiazol-2-yl, 4,5-dimethyl-thiazol-2-yl, benzthiazol-2-yl, 4,5-dimethyl-oxazol-2-yl, 4-phenyl-oxazol-2-yl, oxazolin-2-yl, imidazol-2-yl, imidazolin-2-yl, 1-methyl-imidazolin-2-yl, 2-furyl, 2-thiophenyl, 2-pyrrolyl, 2-thiazolinyl, 3-isoxazolyl, 3-pyrazolyl, thiatriazol-5-yl, purinyl, pyrid-3-yl, pyrid-2-yl, pyrid-4-yl, 5-nitro-pyrid-3-yl, 1-oxidopyrid-2-yl, pyrimid-2-yl, 1,4,5,6- tetrahydropyrimid-2-yl, 4-hydroxy-pyrimid-2-yl, 4-hydroxy-6-methyl-pyrimid-2-yl, 2-hydroxy-pyrimid-4-yl, 2-phenyl-5-ethoxycarbonyl-6-methyl-pyrimid-4-yl, 2-phenyl-5-ethoxycarbonyl-6-ethoxy-pyrimid-4-yl, 2-phenyl-5ethoxycarbonyl-6-amino-pyrimid-4-yl, 2hydroxy-5-cyano-6-methyl-pyrimid-4-yl, 2,6-dimethyl-5-acetyl-pyrimid-4-yl, 2-undecyl-5-acetyl-6-methyl-pyrimid-4-yl, 2,6-dimethyl-5-ethoxycarbonyl-pyrimid-4-yl, triazolopyridyl, pyridazinyl, pyrazinyl, 2-methylmercapto-6-phenyl-1,3,5-triazin-4-yl, 5-methyl-6-hydroxy-1,3,4-triazin-2-yl, 5-phenyl-4H-1,3,4-thiadiazin-2-yl, 5-hydroxy-4H-1,3,4-thiadiazin-2-yl, 3-hydroxy-pyridazin-6-yl and tetrazol-[4,5-b]-pyridazin-6-yl.

The cephem compounds of the general formula II

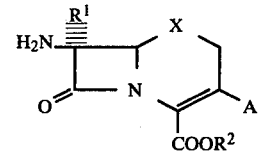

which are to be employed for the reaction according to the invention are known from the literature or can be prepared in accordance with the instructions in the literature, for example in accordance with the instructions in E. F. Flynn, Cephalosporins and Penicillins, Chemistry and Biology, Academic Press, New York and London, 1972, or—when X in formula II represents oxygen or $CH_2$—in accordance with the instructions in J. Amer. Chem. Soc. 96, 7582 and 7584 (1974).

The carboxylic acids of the formula III used for the acylation are novel compounds which can be prepared according to the invention in good yields. The starting point for their preparation is the acetoglyoxylic acid ester, which is accessible from the acetoacetic acid ester in accordance with the instructions in the literature. Preferably, the esters employed are the readily accessible low-molecular alkyl esters, especially the ethyl ester.

Several routes have been described in the literature for the formation of the aminothiazole ring, for example the reaction of chloroketo derivatives with thiourea in accordance with the following equation:

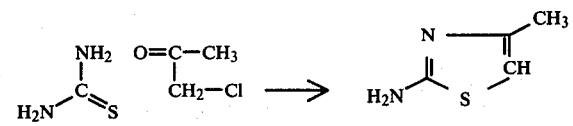

It has now been found, surprisingly, that an acetoglyoxylic acid ester can be converted easily and in high yields to a halogeno-acetoglyoxylic acid ester. Halogenating agents which have proved suitable are especially sulfuryl chloride or elementary bromine.

The bromination is carried out in a solvent. Solvents which have proved suitable are in particular the halogenated hydrocarbons, such as, for example, methylene chloride, chloroform or ethylene dichloride.

The reaction can be carried out within a wide temperature range. In order to achieve high yields of monohalogenoacetoglyoxylic acid ester, a temperature range of $-20°$ to $+20°$ is preferred.

If elementary bromine has been used for the halogenation, the bromoacetoglyoxylic acid ester can be further reacted directly, as the raw material, with thiourea.

In order to achieve good yields it is advisable to employ the thiourea in equimolar amounts. It has been found, surprisingly, that (2-amino-thiazol-4-yl)-glyoxylic acid esters of the formula V form in high yields when the bromoacetoglyoxylic acid ester is reacted with thiourea.

The reaction can be carried out in various ways. A preferred method comprises initially introducing the thiourea in solution and allowing the halogen compound to run into the reaction mixture.

Solvents which have proved suitable for this reaction are mixtures of organic solvents with water. Mixtures of alcohols and water, especially mixtures of ethanol and water, are particularly suitable.

The reaction can be carried out within a wide temperature range, for example at −5° to +80°. The temperature range of 20° to 60° is particularly suitable.

The reaction products of the formula V can be isolated by routes known from the laboratory, for example by evaporating off the organic solvent and subsequently adjusting the pH value to 5-7. The adjustment of the pH value is effected with bases and organic or inorganic bases can be used. For example, the inexpensive alkali metal hydroxides, alkali metal carbonates and alkali metal bicarbonates and the corresponding phosphates have proved suitable.

By means of the reaction which follows the reaction with thiourea, the amino group in the compounds of the formula V is provided with a protective group. Possible protective groups are groups known from the literature, such as, for example, tert.-butoxycarbonyl, carbobenzyloxy, chloroacetyl, trichloroethyl, benzhydryl or formyl. The triphenylmethyl group has proved particularly suitable as a protective group and is introduced by reacting the compounds of the formula V with triphenylchloromethane. The reaction is appropriately carried out in an organic solvent, such as, for example, halogenated hydrocarbons, in the presence of bases. Halogenated hydrocarbons which have proved particularly suitable are chloroform and methylene chloride. Bases which may be mentioned are, in particular, the tertiary amines, such as, for example, triethylamine or N-methylmorpholine.

The esters of the formula VI, which are thus obtained, are saponified to the corresponding acids of the formula III. Mixtures of dioxane and water have proved particularly suitable for the saponification. Thus, it is advantageous to saponify the esters hot in dioxane with the addition of the calculated amount of base and then to isolate the resulting salts. Bases which have proved suitable are, for example, alkali metal hydroxides, especially sodium hydroxide.

The sodium salts formed when sodium hydroxide is used in most cases crystallize out from the reaction mixture on cooling. They can be converted into the acids of the formula III, which are better suited for some activation reactions, by the addition of dilute mineral acids. Acids which may be mentioned for this purpose are, in particular, hydrochloric acid or sulfuric acid.

In other cases, the sodium salts can also be employed direct for the activation.

The carboxylic acids of the general formula III can be converted by processes known from the literature into the activated carboxylic acid derivatives capable of forming an amide. A preferred process for activating the carboxyl group comprises converting it into a symmetrical or unsymmetrical anhydride. The processes for the preparation of mixed or symmetrical anhydrides are known from the literature. For example, chloroformic acid esters or pivaloyl chloride can be used for the activation, in which case the acid of the formula III has to be converted into a corresponding salt. It has been found that the reaction proceeds readily when the acid is suspended in halogenated hydrocarbons, such as, for example, methylene chloride, and converted, using organic bases, such as, for example, triethylamine, into the triethylammonium salt. Alternatively, in some cases it is also possible to employ, for example, alkali metal salts of the acids of the formula III and in this case the addition of catalytic amounts of a tertiary base, such as, for example, N,N-dimethylaniline, has proved advantageous.

The inner anhydrides can also be formed from the carboxylic acids of the formula III using condensing agents, such as, for example, dicyclohexylcarbodiimide, and these inner anhydrides are then reacted with the aminocephem-carboxylic acid derivatives of the formula II.

A further variant comprises employing addition products of the carboxylic acids and condensing agents, such as, for example, dicyclohexylcarbodiimide, for acylating the cephem acids or their esters of the formula II.

The preparation of the compounds of the general formula I can be carried out under various experimental conditions. Thus, for example, the aminocephem derivatives of the formula II can be acylated in very diverse solvents. Suitable solvents are, for example, organic solvents, such as halogenated hydrocarbons, for example methylene chloride or chloroform, but also water or mixtures of water and organic solvents which are miscible with water.

In order to achieve a good course of reaction, it is desirable to bring the aminolactam derivatives into solution.

In the case of the aminocephem esters of the general formula II, the reaction is carried out in organic solvents in which most of the esters are readily soluble. Examples of such solvents which may be mentioned are the halogenated hydrocarbons, such as methylene chloride or chloroform, but also the tertiary amides, such as dimethylformamide or dimethylacetamide.

Esters in the sense of the invention which can be used are, for example, those compounds of the formula II in which $R^2$ represents low-molecular alkyl, preferably tertiary butyl or substituted methyl, in which the methyl group is substituted in particular by trichloromethyl, acyloxy, preferably acetoxy or pivaloyloxy, or by one or two phenyl radicals, which, in turn, can be substituted, for example, by low-molecular alkoxy, preferably methoxy, or the nitro group, or represents the phthalide ester. Examples conforming to the above definitions which may be mentioned are, in particular, the tert.-butyl esters, the trichloroethyl and p-methoxybenzyl esters, the benzhydryl, acetoxymethyl and pivaloyloxymethyl esters or the phthalide esters.

When the aminocephemcarboxylic acids of the general formula II ($R^2$=hydrogen) are used, the compounds must be brought into solution with the addition of bases.

Suitable bases which can be used for dissolving 7-ACA and also a large number of 7-amino-$\Delta^3$-cepem-4-carboxylic acids are inorganic or organic bases. Thus, bases which have proved suitable for the preparation of solutions in organic solvents are in particular the tertiary amines, such as triethylamine, N,N-dimethylaniline or N-methylmorpholine, and those which have proved suitable for preparing aqueous solutions are in particular the alkali metal bicarbonates, such as sodium bicarbonate or potassium bicarbonate, and also the tertiary amines. The bases are in general added in at least the stoichiometric amount, relative to the desired conversion. However, it is advisable to use an excess of base of, for example, about 20 to 80%.

Especially in the case of compounds of the formula II which are sensitive to bases, a constant pH of about 4 to 8, and preferably 6 to 7, depending on the course of the reaction, can be maintained by continuous addition of the base.

The aminolactam derivatives of the formula II can be dissolved within a wide temperature range. In the case of derivatives sensitive to bases, however, it is advisable to choose a temperture range of about 0° to 15°.

The activated glyoxylic acid derivatives of the formula III are added to the amino-cephem derivatives of the formula II, which are in solution or optionally in suspension. The reaction takes place in a manner which is in itself known, at temperatures such as are customary for the preparation of carboxylic acid amides from reactive carboxylic acid derivatives of the formula III.

When water or mixtures of water and organic solvents are used as the reaction medium, it is advisable to maintain a temperature range of about −5° to +10°. When organic solvents are used, the acylation can also be carried out at room temperature.

In order to obtain a better course of reaction, the activated carboxylic acid derivatives of the formula III are taken up in a solvent which does not hinder the reaction and are introduced in diluted form. If the acylation is carried out in an aqueous medium, solvents which can be used for the activated carboxylic acid derivatives are, for example, anhydrous ketones, such as acetone or methyl ethyl ketone, or—with intensive stirring—ethers, such as, for example, diethyl ether or diisopropyl ether.

If the acylation is carried out in a non-aqueous medium, it is advisable to use the same solvent for the dilution of the acid derivatives as is used for the acylation.

In order to obtain high yields, the activated acid derivatives of the formula III are employed in at least the stoichiometric amount. An excess of about 5–25% can prove appropriate.

The acylation products can be isolated by methods which are in themselves known. Thus, for example, the resulting acid derivatives of the formula IV in which $R^2$ represents hydrogen can be taken up, if necessary after evaporating off the organic solvent, in water and precipitated by adding mineral acids. Suitable mineral acids are, in particular, dilute acids, such as dilute hydrochloric acid or sulfuric acid.

In most cases, the amidocephem acids of the formula IV precipitate in the form of amorphous solids or in a crystalline form. They can also be separated as the free acids by extracting at pH 2 to 1. Extraction agents which can be used are diverse water-immiscible organic solvents, for example halogenated hydrocarbons, such as methylene chloride, or esters, such as, for example, ethyl acetate or n-butyl acetate, but also ketones, such as methyl isobutyl ketone.

The resulting amidocephem acids of the formula IV are obtained from the extracts, for example by evaporating off the solvent and grinding the residue, for example with ether.

When the amidocephem compounds of the formula I are prepared from the compounds of the formula IV, the protective group R must be removed. The reaction conditions to be employed depend on the nature of the protective group and are known from the literature.

If, for example, R is a triphenylmethyl group, this group is detached in an acid medium. Mixtures of formic acid and water, especially a mixture of water and formic acid in a ratio of 1:1, have proved suitable. In the case of compounds of the formula IV in which $R^2$ represents, for example, p-methoxybenzyl, benzhydryl or dimethoxybenzyl and R represents a triphenylmethyl group, it is possible simultaneously to detach the ester group and to remove the trityl group by treatment with trifluoroacetic acid/anisole.

The isolation of the amidocephem compounds of the formula I can be effected by known methods. In many cases the resulting compound is dissolved in the reaction medium used, so that an extraction is advisable and, in the case of triphenylmethyl being used as the protective group, the resulting triphenylcarbinol can be filtered off or can be removed with extraction agents, such as, for example, ether.

The amidocephem compounds of the formula I in which $R^2$ represents hydrogen can also be converted to the physiologically acceptable esters of the formula I by subsequent esterification by processes known from the literature. Thus, for example, the acetoxymethyl or pivaloyloxymethyl esters are obtained by reacting the alkali metal salts, preferably the sodium salts, or the ammonium salts, preferably the triethylammonium salts, with the corresponding halogenomethylacyl compounds, such as, for example, chloromethyl acetate, chloromethyl propionate or chloromethyl pivalate.

If the esters, and especially the physiologically acceptable esters, have already been obtained from the acylation, subsequent esterification of the carboxyl group is superfluous.

The esters which are obtained direct from the reaction according to the invention, such as, for example, p-methoxybenzyl, p-nitrobenzyl, tert.-butyl or benzyhydryl esters, can also be converted to the free carboxylic acids of the formula I in a manner known from the literature.

Compounds of the formula I which are in a form suitable for application in human medicine and veterinary medicine are, in particular, those in which $R^2$ represents a physiologically acceptable cation, such as, for example, the alkali metal salts, especially the sodium and potassium salts, or ammonium salts, especially tertiary amine salts, such as, for example, procain salts. The sodium salts are particularly preferred.

If the salts are not isolated direct from the reaction solution, such as, for example, by precipitation with suitable organic solvents, such as, for example, ether, they can also be obtained by reacting the carboxylic acid of the formula I with the desired base, for example sodium hydroxide solution.

In addition to the compounds of the formula I mentioned in the Examples, the following derivatives, for example, can also be prepared by the process according to the invention: 7[(2-aminothiazol-4-yl)-glyoxylamido]-3-cephem-4-carboxylic acid, 7[(2-aminothiazol-4-yl)-glyoxylamido]-3-chloro-3-cephem-4-carboxylic acid, 7[(2-aminothiazol-4-yl)-glyoxylamido]-3-methoxy-3-cephem-4-carboxylic acid, 7[(2-aminothiazol-4-yl)-glyoxylamido]-3-ethoxy-3-cephem-4-carboxylic acid, 7[(2-aminothiazol-4-yl)-glyoxylamido]-3-propoxy-3-cephem-4-carboxylic acid, 7[(2-aminothiazol-4-yl)-glyoxylamido]-3-butoxy-3-cephem-4-carboxylic acid, 7[(2-aminothiazol-4-yl)-glyoxylamido]-3-methyl-thiomethyl-3-cephem-4-carboxylic acid, 7[(2-aminothiazol-4-yl)-glyoxylamido]-3-propyl-thiomethyl-3-cephem-4-carboxylic acid, 7[(2-aminothiazol-4-yl)-glyoxylamido]-3-acetthiomethyl-3-cephem-4-carboxylic acid, 7[(2-aminothiazol-4-yl)-glyoxylamido]-3[(1-propyl-tetrazol-2-yl)-thiomethyl]-3-cephem-4-carboxylic acid, 7[(2-aminothiazol-4-yl)-glyoxylamido]-3[(1-propenyl-tetrazol-2-yl)-thiomethyl]-3-cephem-4-carboxylic acid, 7[(2-aminothiazol-4-yl)-glyoxylamido]-3[(oxazol-2-yl-thiomethyl)-3-cephem-4-carboxylic acid, 7[(2-aminothiazol-4-yl)-glyoxylamido]-3[(5-amino-1,3,4-thiadiazol-2-yl)-thiomethyl]-3-cephem-4-carboxylic acid, 7[(2-aminothiazol-4-yl)-glyoxylamido]-3[(3-methyl-1,2,4-thiadiazol-5-yl)-thiomethyl]-3-cephem-4-carboxylic acid, 7[(2-aminothiazol-4-yl)-glyoxylamido]-3[(4-methyl-thiazol-2-yl)-thiomethyl]-3-cephem-4-carboxylic acid, 7[(2-aminothiazol-4-yl)-glyoxylamido]-3[(1,3,4-thiadiazol-2-yl)-thiomethyl]-3-cephem-4-carboxylic acid, 7[(2-aminothiazol-4-yl)-glyoxylamido]-3[(1,2,4-triazol-5-yl)-thiomethyl]-3-cephem-4-carboxylic acid, 7[(2-aminothiazol-4-yl)-glyoxylamido]-3[(1,2,3-thiadiazol-5-yl)-thiomethyl]-3-cephem-4-carboxylic acid, 7[(2-aminothiazol-4-yl)-glyoxylamido]-3[(1,2,5-thiadiazol-3-yl)-thiomethyl]-3-cephem-4-carboxylic acid, 7[(2-aminothiazol-4-yl)-glyoxylamido]-3[(1,2,3-oxdiazol-5-yl)-thiomethyl]-3-cephem-4-carboxylic acid, 7[(2-aminothiazol-4-yl)-glyoxylamido]-3[(5-methyl-1,3,4-oxadiazol-2-yl)-thiomethyl]-3-cephem-4-carboxylic acid, 7[(2-aminothiazol-4-yl)-glyoxylamido]-3[(5-butyl-1,3,4-oxdiazol-2-yl)-thiomethyl]-3-cephem-4-carboxylic acid, pivaloyloxymethyl 7[(2-aminothiazol-4-yl)-glyoxylamido]-cephalosporanate, 7[(2-aminothiazol-4yl)-glyoxylamido]-cephalosporanic acid phthalide ester, acetoxymethyl 7[(2-aminothiazol-4-yl)-glyoxylamido]-cephalosporanate, 7[(2-aminothiazol-4-yl)-glyoxylamido]-3[(pyrid-2-yl N-oxide)-thiomethyl]-3-cephem-4-carboxylic acid and 7[(2-aminothiazol-4-yl)-glyoxylamido]-3[(3-hydroxy-pyradiazin-6-yl)-thiomethyl]-3-cephem-4-carboxylic acid.

The amidocepehm derivatives of the formula I are valuable antibiotics which are surprisingly well suited for combating Gram-positive and in particular Gram-negative infections and, moreover, also have an unexpectedly good action against penicillinase-forming staphylococci.

The compounds according to the invention can be employed as such or together with the auxiliaries and additives customarily employed therapeutically, such as, for example, tragacanth, lactose, talc, solvents and the like, in the form of galenic formulations, such as, for example, tablets, dragées, capsules, suspensions, solutions and the like, perorally or preferably, however, parenterally, and as a rule an administration unit contains the active compound in an amount of about 50 to 1,000 mg, preferably about 100 to 500 mg.

For parenteral use, the solvents known for therapeutic use, especially a solution in water, can be used.

It is also possible to combine the compounds according to the invention with other active compounds. Thus, for example, other antibiotics can be administered, such as, for example, those from the series comprising the penicillins and cephalosporins, or compounds which influence the symptoms of bacterial infections, such as, for example, antipyretic agents, antiphlogisticagents or analgesics.

The illustrative examples which follow serve to further illustrate the invention but do not restrict it thereto.

Preparation of the starting compound (a) Ethyl bromoacetoglyoxylate 120 g of ethyl acetoglyoxylate are dissolved in 700 ml of methylene chloride and reacted in the course of 1 hour at 5° with a solution of 146 g of bromine in 200 ml of methylene chloride.

After the solution has become decolorized, the solvent was stripped off and the residual oil was reacted without further purification.

(b) Ethyl 2-amino-thiazol-4-ylglyoxylate 195 g of ethyl bromoacetoglyoxylate are added dropwise at 5° to a solution of 66 g of thiourea in 450 ml of water and 450 ml of ethanol; after the addition is complete, the mixture is stirred for 30 minutes at room temperature and for 30 minutes at 50° and the resulting reaction mixture is then filtered after adding active charcoal. The pH of the filtrate is brought to 7 by adding sodium bicarbonate solution, whereupon ethyl 2-amino-thiazol-4-yl-glyoxylate crystallizes out as crystals having a melting point of 147°.

(c) Ethyl 2-triphenylmethylamino-thiazol-4-yl-glyoxylate 27 g of triethylamine are added to a solution of 90 g of ethyl 2-aminothiazol-4-glyoxylate in 225 ml of dimethylformamide and 375 ml of $CH_2Cl_2$, at $-15°$, and 75 g of triphenylchloromethane are then added at $-30°$. After 15 minutes at $-30°$, the mixture is stirred for 3 hours without a cooling bath, 500 ml of $CH_2Cl_2$ are added to the resulting reaction mixture and the mixture is washed with 300 ml of 1 N HCl and then twice with 200 ml of water, The organic phase is dried over $Na_2SO_4$ and the solvent is evaporated off. An oil remains and this was used for the further reactions without prior purification.

(d) 2-Triphenylmethylamino-thiazol-4-yl-glyoxylic acid

A solution of 14.8 g of NaOH in 370 ml of methanol is added to a solution of 156 g of crude ethyl 2-triphenylamethylamino-thiazol-4-yl-glyoxylate in 150 ml of methanol and the mixture is boiled under reflux for 5 minutes, whereupon the sodium salt of 2-triphenylmethylamino-thiazol-4-yl-glyoxylic acid crystallizes out.

The sodium salt obtained is suspended in 380 ml of water and 76 ml of 2 N HCl are added, while stirring vigorously. After 15 minutes the precipitate is filtered off, washed with water and dried.

2-Triphenylmethylamino-thiazol-4-yl-glyoxylic acid is obtained in the form of yellow crystals having a melting point of 163°–165° (decomposition).

The Rf values indicated in the Examples which follow were determined by thin layer chromatography on silica gel ready-to-use plates 60 F 254 from Messrs. Merck, Darmstadt.

EXAMPLE 1

7[(2-Triphenylmethylamino-thiazol-4-yl)-glyoxylamido]-cephalosporanic acid (a) 2.4 g of triethylamine are added to a suspension of 9.1 g of (2-triphenylmethylamino-thiazol-4-yl)-glyoxylic acid in 50 ml of methylene chloride, the resulting solution is cooled to $-50°$ under nitrogen and with the exclusion of moisture and a solution of 2.66 g of pivaloyl chloride in 200 ml of methylene chloride is added.

After the addition is complete, the mixture is stirred for a further 2 hours at 0°, the solution of the mixed anhydride is then again cooled to $-50°$ and a solution of 5.44 g of 7-aminocephalosporanic acid in a mixture of 50 ml of methylene chloride and 4.04 g of triethylamine is added.

After the addition is complete, the mixture is stirred for a further 3 hours without a cooling bath, the solvent is then stripped off in vacuo, the residue is taken up in 500 ml of water and the solution is acidified to pH 1 with 2 N HCl and immediately taken up several times in methylene chloride. After drying, the organic phase is removed and the residue is around with ether. 7[(2-Triphenylmethylamino-thiazol-4-yl)-glyoxylamido]-cephalosporanic acid is isolated as a solid product.

Rf (butanol, H$_2$O, ethyl alcohol, acetic acid, 5:2:1.5:1.5) 0.53

IR in KBr: lactam CO:1,780 cm$^{-1}$ (b)
7[(2-Aminothiazol-4-yl)-glyoxylamido]-cephalosporanic acid If the 7-((2-triphenylmethylamino-thiazol-4-yl)-glyoxylamido)-cephalosporanic acid obtained according to a) is reacted under the conditions indicated in Example 3b), this gives 7[(2-aminothiazol-4-yl)-glyoxylamido]-cephalosporanic acid in the form of yellow crystals.

Rf (conditions as in Example 1) : 0.38
IR in KBr: lactam CO : 1,776 cm$^{-1}$

EXAMPLE 2

(a)
7[(2-Triphenylmethylamino-thiazol-4-yl)-glyoxylamido]-3[(5-methyl-1,3,4-thiadiazol-2-yl)-thiomethyl]-3-cephem-4-carboxylic acid.

In the manner indicated in Example 1 a), 7[(2-triphenylmethyl-amino-thiazol-4-yl)-glyoxylamido]-3[(5-methyl-1,3,4-thiadiazol-2-yl)-thiomethyl]-3-cephem-4-carboxylic acid is obtained as a solid using 7-amino-3-[(5-methyl-1,3,4-thiadiazol-2-yl)-thiomethyl]-3-cephem-4-carboxylic acid.

Rf (conditions as in Example 1):0.58
IR in KBr : lactam CO :1,780 cm$^{-1}$ (b)
7[(2-Amino-thiazol-4-yl)-glyoxylamido]-3[(5-methyl-1,3,4-thiadiazol-2-yl)-thiomethyl]-3-cephem-4-carboxylic acid Analogously to Example 3b), 7[(2-amino-thiazol-4-yl)-glyoxylamido]-3(5-methyl-1,3,4-thiadiazol-2-yl)-thiomethyl]-3-cephem-4-carboxylic acid is obtained from the 7[(2-triphenylmethylaminothiazol-4-yl)-glyoxylamido]-3[(5-methyl-1,3,4-thiadiazol-2-yl)-thiomethyl]-3-cephem-4-carboxylic acid prepared according to a).

Rf (conditions as in Example 1):0.39
IR: in KBr: lactam CO:1,770 cm$^{-1}$ 100 ml of methylene chloride were added to a suspension of 2.8 g of the sodium salt of 2-triphenylmethylamino-thiazol-4-yl glyoxylic acid in 20 ml of water, the aqueous solution was acidified to pH 1 and 2 N HCl and the acid which precipitated out was extracted.

After repeated extraction, the combined extracts were dried and the solvent was removed in vacuo. 40 ml of methylene chloride and 0.63 g of triethylamine were added to the oily residue, the resulting solution was cooled to $-25°$ and reacted with a solution of 0.75 g of pivaloyl chloride in 20 ml of methylene chloride to give the mixed anhydride and the reaction mixture was stirred for a further 2 hours at $+5°$.

The solution was then cooled to $-30°$ and reacted with a solution which had been prepared from 3.14 g of the p-toluene-sulfonate of p-methoxybenzyl 7-amino-3-methyl-3-cephem-4-carboxylate by extraction with 50 ml of methylene chloride at pH 8.

After 1 hour the cooling bath was removed, the mixture was stirred for a further hour at room temperature and the organic solvent was then removed in vacuo.

The residual oil was ground with ether. p-Methoxybenzyl 7[(2-triphenylmethylamino-thiazol-4-yl)-glyoxylamido]-3-methyl-3-cephem-4-carboxylate is isolated as a beige-colored solid.

Rf (in CHCl$_3$/ethyl acetate, 3:1):0.635
IR in KBr: lactam CO:1,775 cm$^{-1}$ (b)
7[(2-Aminothiazol-4-yl)-glyoxylamido]-3-methyl-3cephem-4-carboxylic acid 2.5 g of the p-methoxybenzyl 7[(2-triphenylmethylaminothiazol-4-yl)-glyoxylamido]-3-methyl-3-cephem-4-carboxylate prepared according to (a) are dissolved in 7.5 ml of anisole, 2.5 ml of CF$_3$COOH are added to the solution and the reaction mixture is stirred for 5 hours at 25°–30°.

The reaction mixture is then concentrated to dryness, the residue is ground with ether and the solid product is isolated.

The solid is stirred with 10 ml of methylene chloride for 30 minutes at room temperature and free 7[(2-aminothiazol-4-yl)-glyoxylamido]-3-methyl-3-cephem-4-carboxylic acid is obtained.

IR in KBr: lactam CO:1,763 cm$^{-1}$

EXAMPLE 5

The sodium salt of 7[(2-aminothiazol-4-yl)-glyoxylamido]-cephalosporanic acid 5 g of Na acetate are added to a suspension of 10 g of the 7[(2-amino-thiazol-4-yl)-glyoxylamido]-cephalosporanic acid obtained according to Example 1 in 50 ml of CH$_3$OH and the acid briefly goes into solution. After a short time the pale yellow sodium salt of 7[(2-aminothiazol-4-yl)-glyoxylamido]-cephalosporanic acid crystallizes out.

Rf (conditions as in Example 1): 0.38
IR in KBr: lactam CO:1,745 cm$^{-1}$

EXAMPLE 6

The sodium salt of 7[(2-aminothiazol-4-yl)-glyoxylamido]-3[(1-methyl-tetrazol-2-yl)-thiomethyl]-3-cephem-4-carboxylic acid In the manner indicated in Example 5, the sodium salt of 7[(2-aminothiazol-4-yl)-glyoxylamido]-3-[(1-methyl-tetrazol-2-yl)-thiomethyl]-3-cephem-4-carboxylic acid is obtained in the form of yellow crystals from the cephem acid prepared in Example 3.

Rf (conditions as in Example 1): 0.40
IR in KBr: lactam CO:1,755 cm$^{-1}$

EXAMPLE 7

Benzhydryl 7[(2-triphenylmethylaminothiazol-4-yl)-glyoxylamido]-7-methoxy-cephalosporanate 2.2 g of triethylamine are added to a suspension of 4.1 g of (2-triphenylmethylamino-thiazol-4-yl)-glyoxylic acid in 30 ml of methylene chloride, whereupon the acid goes into solution. The resulting solution is cooled to $-30°$ with the exclusion of moisture and a solution of 2.66 g of pivaloyl chloride in 20 ml of methylene chloride is added.

After the addition is complete, the reaction mixture is stirred for a further 60 minutes and then again cooled to −50° and a solution of 4.0 g of benzhydryl 7-amino-7-methoxycephalosporanate in 30 ml of methylene chloride is added.

After the addition is complete, the cooling bath is removed, the mixture is stirred for 4 hours at room temperature and then for 1 hour under reflux, the organic solvent is then removed and ether is added to the residue. Benzhydryl 7[(2-triphenylmethylaminothiazol-4-yl)-glyoxylamido]-7-methoxycephalosporanate separates out as a yellow-brown solid.

IR in KBr: lactam CO:1,780 cm$^{-1}$
Rf (conditions as in Example 4): 0.68

The elimination of the protective group and simultaneous saponification are effected as indicated in Example 4.

We claim:

1. A cephem compound of the formula

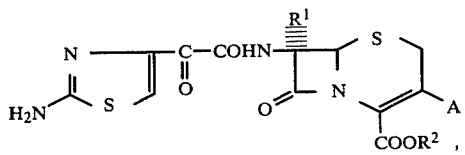

wherein
R$^1$ is hydrogen or low-molecular alkoxy;
R$^2$ is hydrogen, phthalide, a physiologically acceptable cation, low-molecular alkyl, or methyl substituted by trichloromethyl, by alkanoyloxy, by phenyl, by nitrophenyl, or by low-molecular alkoxyphenyl; and
A is hydrogen, alkoxy, halogen, or —CH$_2$Y wherein Y is hydrogen, alkanoyloxy, alkoxy, carbamoyloxy, or —SR$^3$ wherein R$^3$ is low-molecular alkanoyl, alkyl, a 5-membered ring having 1 to 4 nitrogen atoms, a 5 membered ring having 1 or 2 nitrogen atoms and an oxygen atom or a sulfur atom, a 6-membered ring having 1 or 2 nitrogen atoms, a 6-membered ring having 1 or 2 nitrogen atoms and a sulfur atom, or R$^3$ is such a 5-membered or 6-membered ring substituted by straight-chain or branched alkyl having 1 to 8 carbon atoms, by phenyl, or by phenyl which in turn is substituted by low-molecular alkyl, by low-molecular alkoxy, by nitro, or by halogen.

2. A compound as in claim 1 wherein R$^1$ is hydrogen, R$^2$ is hydrogen, and A is —CH$_2$OCOCH$_3$.

3. A compound as in claim 1 wherein R$^1$ is hydrogen R$^2$ is hydrogen, and A is

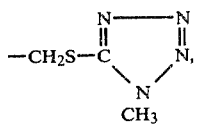

4. A pharmaceutical composition active against bacterial infections comprising an anti-bacterially effective amount of a compound as in claim 1 and a pharmaceutical carrier therefor.

5. The method for treating a bacterial infection in a patient suffering therefrom which comprises administering to said patient an anti-bacterially effective amount of a compound as in claim 1.

* * * * *

Disclaimer 4,201,779.—*Dieter Bormann* and *Bernd Knabe*, Kelkheim; *Elmar Schrinner* and *Manfred Worm*, Wiesbaden, all of Fed. Rep. of Germany. 7[(2-AMINO-THIAZOL-4-YL) GLYOXYLAMIDO]-CEPHEM DERIVATIVES AND PROCESSES FOR THEIR PREPARATION. Patent dated May 6, 1980. Disclaimer filed Dec. 22, 1980, by the assignee, *Hoechst Aktiengesellschaft*.

Hereby enters this disclaimer to claims 1, 2, 3, 4, and 5 of said patent.

[*Official Gazette March 10, 1981.*]

UNITED STATES PATENT AND TRADEMARK OFFICE
CERTIFICATE OF CORRECTION

PATENT NO. : 4,201,779  
DATED : May 6, 1980  
INVENTOR(S) : Bormann et al.

It is certified that error appears in the above-identified patent and that said Letters Patent are hereby corrected as shown below:

In Column 13, after line 51 reading "IR: in KBr: lactam CO:1,770 $cm^{-1}$" insert:

--Example 3:

a) 7[(2-Triphenylmethylamino-thiazol-4-yl)-glyoxylamido]-3[(1-methyl-tetrazol-2-yl)-thiomethyl]-3-cephem-4-carboxylic acid In the manner indicated in Example 1 a), 7[(2-triphenylmethylamino-thiazol-4-yl)-glyoxylamido]-3[(1-methyl-tetrazol-2-yl)-thiomethyl]-3-cephem-4-carboxylic acid is obtained as a solid using 7-amino-3((1-methyl-tetrazol-2-yl)-thiomethyl)-3-cephem-4-carboxylic acid.

Rf (conditions as in Example 1) : 0.56  
IR in KBr : lactam CO : 1,772 $cm^{-1}$ b) 7[(2-Aminothiazol-4-yl)-glyoxylamido]-3[(1-methyl-tetrazol-2-yl)-thiomethyl]-3-cephem-4-carboxylic acid 14 g of the 7[(2-triphenylmethylamino-thiazol-4-yl)-glyoxylamido)-3-((1-methyl-tetrazol-2-yl)-thiomethyl)-3-cephem-4-carboxylic acid prepared according to a) are introduced into a mixture of 30 ml of formic acid and 30 ml of water, the reaction mixture is warmed to 50 - 60° for 30 minutes and cooled, 100 ml of water are added and the triphenylcarbinol

UNITED STATES PATENT AND TRADEMARK OFFICE
CERTIFICATE OF CORRECTION

PATENT NO. : 4,201,779
DATED : May 6, 1980
INVENTOR(S) : Bormann et al.

It is certified that error appears in the above-identified patent and that said Letters Patent are hereby corrected as shown below:

which has been split off is filtered off.

The filtrate was evaporated to dryness and the residue was ground with ether. This gives 7[(2-aminothiazol-4-yl)-glyoxylamido]-3[(1-methyl-tetrazol-2-yl)-thiomethyl]-3-cephem-4-carboxylic acid in the form of a pale yellow solid.
IR in KBr : lactam CO : 1,775 $cm^{-1}$ Example 4:

a) p-Methoxybenzyl 7[(2-triphenylmethylamino-thiazol-4-yl)-glyoxylamido]-3-methyl-3-cephem-4-carboxylate.--

Signed and Sealed this

Twenty-second Day of September 1981

[SEAL]

Attest:

Attesting Officer

GERALD J. MOSSINGHOFF

Commissioner of Patents and Trademarks